United States Patent [19]

Reddy et al.

[11] Patent Number: 5,989,879
[45] Date of Patent: Nov. 23, 1999

[54] COMPOSITIONS AND METHODS USING EUKARYOTIC RAD52

[75] Inventors: Gurucharan Reddy, Redwood City, Calif.; Efim Ilya Golub, New Haven; Charles Meyer Radding, Hamden, both of Conn.

[73] Assignee: Yale University, New Haven, Conn.

[21] Appl. No.: 08/781,329

[22] Filed: Jan. 10, 1997

Related U.S. Application Data

[60] Provisional application No. 60/029,055, Oct. 24, 1996.

[51] Int. Cl.[6] ............................ C12N 15/63; C12N 21/06; C07K 13/00; C07H 21/04
[52] U.S. Cl. ............................ 435/172.3; 435/6; 530/350; 536/23.1
[58] Field of Search .................... 435/6, 172.3; 530/350; 536/23.1

[56] References Cited

PUBLICATIONS

Panyutin and Hsieh, "Formation of a Single Base Mismatch Impedes Spontaneous DNA Branch Migration," *J. Mol. Biol.*, 230:413–424 (1993).
Reddy et al., "Human Rad52 protein promotes single-strand DNA annealing followed by branch migration," *Database Medline—NLM, Mutation Research*, Netherlands, AN 97363253 (Jun. 1997).
New et al., "Rad52 protein stimulates DNA strand exchange by Rad51 and replication protein A, " Nature (London), 391:401–410 (Jan. 1998).
Ogawa, T., et al., "A Species–Specific Interaction of Rad51 and Rad52 Proteins in Eukaryotes", *Adv. Biophys.* vol. 31:93–100 (1995).
Park, M.S., et al., "Physical Interaction Between Human RAD52 and RPA is Required for Homologous Recombination in Mammalian Cells", *The Journal of Biol. Chem.* vol. 271(31):18996–19000 (1996).
Shen, Z., et al., "The Human and Mouse Homologs of the Yeast RAD52 Gene: cDNA Cloning, Sequence Analysis, Assignment to Human Chromosome 12p 12.2–p13, and mRNA Expression in Mouse Tissues", *Genomics* 25:199–206 (1995).
Bendixen, C., et al., "Identification of a Mouse Homologue of the *Saccharomyces cerevisiae* Recombination and Repair Gene, RAD52", *Genomics* 23:300–303 (1994).
Ogawa, T., et al., "RecA–like Recombination Proteins in Eukaryotes:Functions and Structures of RAD51 Genes", *Cold Spring Harbor Symposia on Quantitative Biology*, vol. LVIII.:567–576 (1993).
Park, M.S., "Expression of Human RAD52 Confers Resistance to Ionizing Radiation in Mammalian Cells", *The Journal of Biological Chemistry*, vol. 270(26):15467–15470 (1995).
Bezzubova, O.Y., et al.,"Identification of a Chicken RAD52 Homologue Suggests Conservation of the RAD52 Recombination Pathway Throughout the Evolution of Higher Eukaryotes", *Nucleic Acids Research* 21(25:5945–5949 (1993).

Smith, J., et al., "A Mutation in the Gene Encoding the *Saccharomyces cerevisiae* Single–Stranded DNA–Binding Protein Rfal Stimulates a RAD52–Independent Pathway for Direct–Repeat Recombination", *Molecular and Cellular Biology*, vol. 15(3):1632–1641 (1995).
Sugawara, N., et al., "DNA Structure–DependentRequirements for Yeast RAD Genes in Gene Conversion", *Nature*, vol. 373:84–86 (1995).
Rattray, A.J. et al., "Use of a chromosomal Inverted Repeat to Demonstrate that the RAD51 and RAD52 Genes of *Saccharomyces cerevisiae* Have Different Roles in Mitotic Recombination", *Genetics* 138:587–595 (1994).
Hays, S.L., et al., "Complex Formation in Yeast Double–Strand Break Repair: Participation on Rad51, Rad52, Rad55, and Rad57 Proteins", *Proc. Natl. Acad. Sci, USA, Genetics* vol. 92:6925–6929 (1995).
Shinohara, A., et al., "Homologous Recombination and the Roles of Double–Strand Breaks", *TIBS* 20:387–391 (1995).
Johnson, R.D., et al., "Functional Differences and Interactions Among the Putative RecA Homologs Rad51, Rad52, and Rad57", *Molecular and Cellular Biology* 4843–4850 (1995).
Milne, G.T., et al., "Dominant Negative Alleles of RAD52 Reveal a DNA Repair/Recombination Complex Including Rad51 and Rad52", *Genes & Development* 1755–1765 (1993).
Adzuma, K. et al., "Primary Structure of the RAD52 Gene in *Saccharomyces cerevisiae*", *Molecular and Cellular Biology* vol. 4(12):2735–2744 (1984).
Donovan, J.W., et al., "Homotypic and Heterotypic Protein Associations Control Rad51 Function in Double–Strand Break Repair", *Genes & Development* 2552–2562 (1994).
Shen, Z., et al., "Specific Interactions Between the Human RAD51 and RAD52 Proteins", *The Journal of Biological Chemistry* vol. 271(1):148–152 (1996).
Klein, H.L., "Genetic Control of Intrachromosomal Recombination", *BioEssays* vol. 17(2):147–159 (1995).
Haber, J.E., "In vivo biochemistry: Physical monitoring of recombination induced by site–specific endonucleases", *BioEssays* vol. 17(7):609–620 (1995).
Mortensen et al. DNA strand annealing is promoted by the yeast Rad52 protein. PNAS (USA) vol. 93:10729–10734, Oct. 1, 1996.
Sugawara et al. Characterization of double–strand break–induced recombination: Homology requirements and single–stranded DNA formation. Mol. Cell. Biol. vol. 12(2):563–575, Feb. 1992.
Muris et al. Cloning of human and mouse genes homologous to Rad52, ayeast gene involved in DNA repair and recombination. Mut. Res., DNA Repair. vol. 315:295–305, Dec. 1994.

*Primary Examiner*—James Ketter
*Assistant Examiner*—William Sandals
*Attorney, Agent, or Firm*—Flehr Hohbach Test Albritton & Herbert LLP; Richard F. Trecartin; Robin M. Silva

[57] ABSTRACT

The invention relates to complexes of eukaryotic Rad52 protein and nucleic acids, and methods of using the complexes.

23 Claims, 1 Drawing Sheet

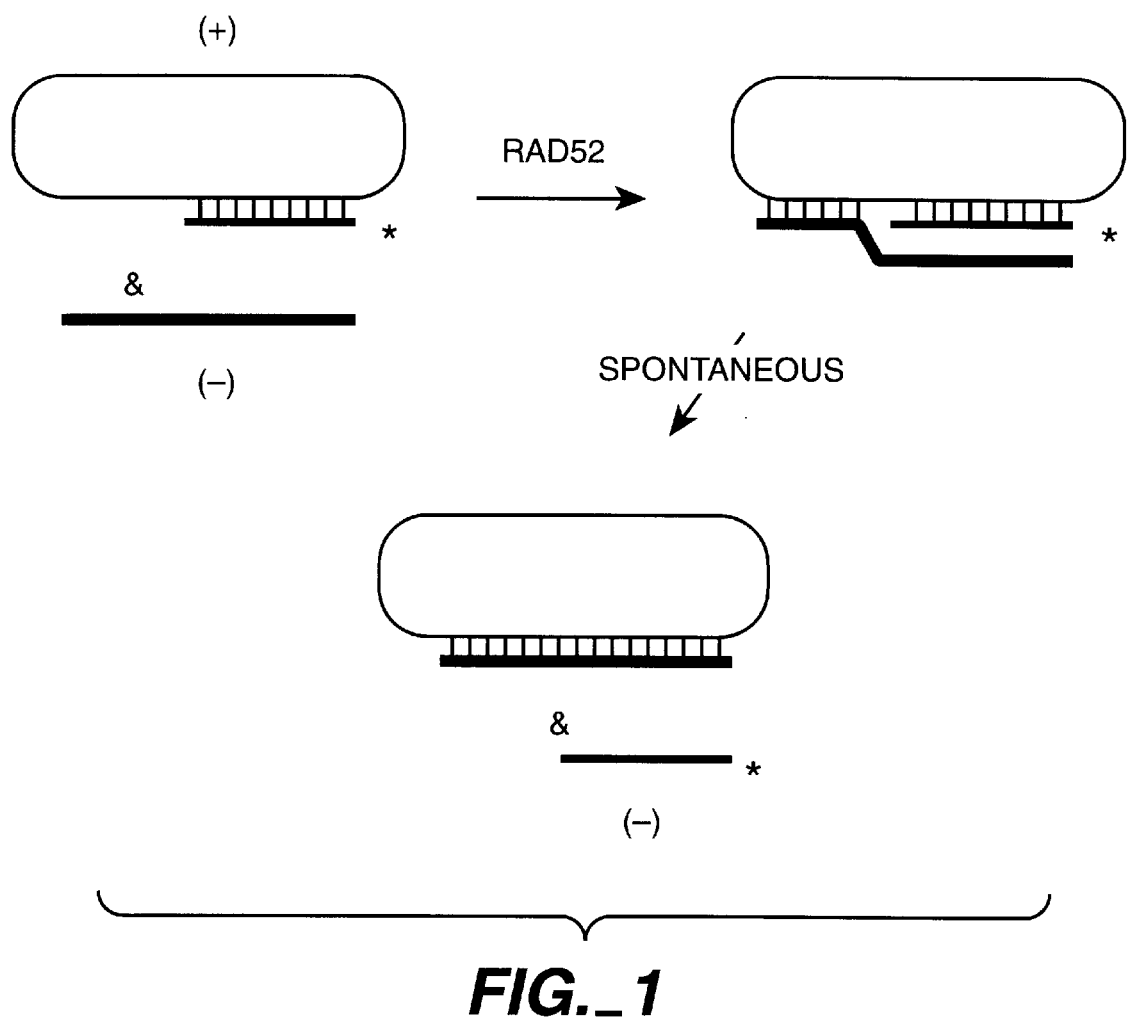
FIG._1

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 32 base pairs
      (B) TYPE: nucleic acid
      (C) STRANDEDNESS: unknown
      (D) TOPOLOGY: unknown (ii) MOLECULE TYPE: DNA (xi) SEQUENCE DESCRIPTION: SEQ ID NO:1:

CGCGGATCCG ATGTCTGGGA CTGAGGAAGC AA                           32

(2) INFORMATION FOR SEQ ID NO:2:

(i) SEQUENCE CHARACTERISTICS:
        (A) LENGTH: 28 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO:2:

GTAGGATCCT GAGCCTCAGT TAAGATGG                                28

COMPOSITIONS AND METHODS USING EUKARYOTIC RAD52

This application claims benefit to provisional application Ser. No. 60/029,055 Oct. 24, 1996.

FIELD OF THE INVENTION

The invention relates to complexes of eukaryotic Rad52 protein and nucleic acids, and methods of using the complexes.

BACKGROUND OF THE INVENTION

Repair of DNA damage is critical for the maintenance of genome integrity and cell survival. Living organisms have developed different pathways of DNA repair to deal with various types of DNA damage. One of the pathways of repairing DNA damage is through homologous recombination. The RecA protein of *E. coli* has been shown to be important for homologous recombination, and a great deal is known about this process in *E. coli*.

Although eukaryotic cells have RecA homologue(s), the mechanism of homologous recombination in vivo are poorly understood in eukaryotes. There is no evidence yet that eukaryotic cells employ RecA-like recombination mechanisms in vivo.

In the yeast *S. cerevisiae*, three epistasis groups of DNA damage-repair genes have been identified (Friedberg, E. C., Siede, W. and Cooper, A. J. (1991) in *The Molecular and Cellular Biology of the yeast Saccharomyces* (Broach, J. R., Pringle, J. R., Jones, E. W., eds) pp 147–192, Cold Spring Harbor Laboratory press, Plainview, N.Y.; Game, J. (1983) in *Yeast Genetics: Fundamental and Applied Aspects* (Spencer, J. F. T., Spencer, D., and Smith., A. R. W., eds) pp 105–137, Springer-verlag, New York.). The Rad52 epistasis group, which is mainly responsible for double-strand break (DSB) repair contains several genes: Rad50–Rad57, MRE11 and XRS2. Among these genes, mutations in Rad51, Rad52 and Rad54 cause the most severe and pleiotropic defects (Game, J. (1983) in *Yeast Genetics: Fundamental and Applied Aspects* (Spencer, J. F. T., Spencer, D., and Smith., A. R. W., eds) pp 105–137, Springer-verlag, New York.; Ajimura, M., Leem, S. H. and Ogawa, H. (1993) *Genetics* 133, 51–66; Ivanov, E. L., Korolev, V. G. and Fabre, F. (1992) *Genetics* 132, 651–664; Petes, T. D., Malone, R. E. and Symington, 1. S. (1991) 407–521.). Yeast strains lacking a functional Rad52 gene are extremely X-ray sensitive and deficient in mitotic and meiotic recombination (Resnick, M. A. (1969) *Genetics* 62, 519–531). It was reported recently that the overexpression of human Rad52 (HsRad52) conferred enhanced resistance to gamma rays and induced homologous intrachromosomal recombination in cultured monkey cells (Park, M. S. (1995) *J. Biol. Chem.* 270, 15467–15470). Mutations in different regions of Rad52 often result in different phenotypes (Boundy-Mills, K. and Livingston, D. M. (1993) Genetics 133, 39–49). It is proposed that the product of Rad52 gene is not required for the initiation of recombination, but is essential for an intermediate stage following the formation of DSBs but before the appearance of stable recombinants (Shinohara, A., Ogawa, H. and Ogawa, T. (1992) *Cell* 69, 457–470).

In the yeast *S. cerevisiae*, the major pathway of double-strand break repair is through gap repair, leading to gene conversion that may be associated with a crossover of flanking markers (Szostak, J. W., Orr-weaver, T. L., Rothstein, R. J. and Stahl, F. W. (1983) *Cell* 33, 25–35). Both Rad51 and Rad52 are important for the repair of breaks by this mechanism. However, gene conversion is only one of several homologous and non-homologous recombination pathways that are found in yeast and mammalian cells to repair chromosomal DSBs (Haber, J. E. (1995) *BioEssays* 17, 609–620). Based on transformation experiments in mammalian cells and in Xenopus oocytes, single-strand annealing, a non-conservative mechanism, has been proposed as an alternate pathway to repair double-strand breaks. (Fishman-Lobell, J., Rudin, N. and Haber, J. E. (1992) *Mol. Cell Biol.* 12, 1292–1303; Lin, F. -L. M., Sperle, K. and Sternberg, N. (1990) *Mol. Cell. Biol.* 10, 103–112; Maryon, E. and Carrol, D. (1991) *Mol. Cell. Biol.* 11, 3278–3287; Jeongyu, S. J. and Carrol, D. (1992) *Mol. Cell. Biol.* 12, 112–119.). Rad52 appears to be important for all homologous recombination events including gene conversion and single-strand annealing.

Despite the importance of Rad52 for homologous recombination the repair of chromosomal breaks, there is very little information available on the biochemistry of Rad52 protein. Homologs of Rad52 gene have been found in several eukaryotic organisms including yeast, mouse, chicken and human (see Park, J. Biol. Chem. 270:15467–15470 (1995); Muris et al., Mutation Res., DNA Repair 315:295–305 (1994); Bezzubova et al., Nucleic Acid Res. 21(25):5945–5949 (1993); Bendixen et al., Genomics 23:300–303 (1994); Shen et al., Genomics 25:199–206 (1995)).

Sequence analysis has revealed that N-terminal amino acid sequence of Rad52 protein is highly conserved while the C-terminal region is less conserved (Bezzubova, O., Schmidt, H., Ostermann, K., Heyer, W. D. and Buerstedde, J. -M. (1993) *Nucleic Acids Res.* 21, 5945–5949; Muris, D. F. R., Vreeken, K., Carr, A. M., Broughton, B. C., Lehman, A. R., Lohman, P. H. M. and Pastnik, A. (1993) *Nucleic Acids Res.* 21, 4586–4591; Bendixen, C., Sunjevaric, I., Bauchwitz, R. and Rothstein, R. (1994) *Genomics* 23, 300–303; Shen, Z., Denison, K., Lobb, R., Gatewood, J. M. and Chen, D. J. (1995) *Genomics* 25, 199–206).

It has been shown that Rad52 protein interacts through its C-terminal domain with the N-terminal domain of Rad51 protein in a species specific manner (Milne, G. T. and Weaver, D. T. (1993) *Genes & Dev* 7, 1755–176514; Donovan, J. W., T., M. G. and Weaver, D. T. (1994) *Genes & Dev* 8, 2552–2562; Shen, Z., Cloud, K. G., Chen, D. J. and Park, M. S. (1996) *J. Biol. Chem.* 271, 148–152). Similarly, a specific interaction with RPA has also been shown to be important for homologous recombination (see Park et al., J. Biol. Chem. 271(31):18996–19000 (1996)).

Yeast Rad52 protein has been reported to bind to both single and double-stranded DNA and carries out annealing of homologous single-stranded DNA. (Ogawa, T., Shinohara, A., Nabetani, A., Ikeya, T., Yu, X., Egelman, E. H. and Ogawa, H. (1993) *Cold Spring Harbor Symp Quant. Biol.* 58, 567–576.). Besides the report that human Rad52 protein interacts with human Rad51 protein and RPA, there are no other biochemical reports on the function of human Rad52 protein to date.

SUMMARY OF THE INVENTION

The present invention provides compositions comprising complexes of a first single stranded nucleic acid and isolated Rad52 protein from a higher eukaryote. The compositions are capable of mediating the annealing of said first nucleic acid to a complementary second single stranded nucleic acid.

Further provided are compositions further comprising a second single stranded nucleic acid complexed with isolated Rad52 protein from a higher eukaryote. The first and second nucleic acids may be complementary.

Additionally provided are compositions further comprising a double stranded nucleic acid comprising second and third single stranded nucleic acids. Both the first and third nucleic acids are complementary to the second nucleic acid.

Further provided are methods of making double stranded nucleic acid. The method comprises the step of contacting a) a first single stranded nucleic acid; b) a second single stranded nucleic acid, and c) isolated Rad52 protein from a higher eukaryote. The first and second nucleic acids are complementary, such that the Rad52 mediates annealing of the first and second nucleic acids.

Also provided are methods of accomplishing strand exchange comprising contacting: a) a first single stranded nucleic acid; a double stranded nucleic acid comprising second and third single stranded nucleic acids, wherein both the first and third nucleic acids are complementary to the second nucleic acid; and c) isolated Rad52 from a higher eukaryote, under conditions whereby said Rad52 mediates the annealing of the first nucleic acid to the second nucleic acid, such that the third nucleic acid is displaced.

Methods of screening for a bioactive agent involved in homologous recombination are also provided. The methods comprise contacting: i) a candidate bioactive agent; ii) a first single stranded nucleic acid; and iii) isolated Rad52 protein from a higher eukaryote, and then screening for binding of the candidate and the Rad52 to the nucleic acid.

Further provided are methods of screening for a bioactive agent involved in homologous recombination comprising adding: i) a candidate bioactive agent; ii) a first single stranded nucleic acid; and iii) isolated Rad52 protein from a higher eukaryote, to form a mixture. The mixture is then screened for altered biological activity, when compared to the biological activity of the composition in the absence of the candidate.

BRIEF DESCRIPTION OF THE DRAWINGS

FIG. 1 depicts the design of the experiment. A labeled 43-mer oligonucleotide that had been thermally annealed to single-stranded circular M13 DNA to form a partial duplex was displaced in the presence of HsRad52 protein by an overlapping 63-mer, called the donor strand, that had 20 extra nucleotide residues at its 5' end. (See Panyutin et al., J. Mol. Biol., 1993). The asteric indicates a labeled strand. The partial duplex of M13 plus a 43-mer was incubated with an excess of a 63-mer that had been incubated with HsRad52 protein. Displacement of the 32P-labeled 43-mer was detected by agarose gel electrophoresis.

DETAILED DESCRIPTION OF THE INVENTION

In prokaryotes, the RecA mediated homologous recombination reaction is well-documented. This reaction requires only the presence of the RecA protein, which binds to DNA, placing the DNA in an extended, activated conformation which then pairs with homologous duplex DNA and performs strand exchange resulting in recombination. However, the mechanisms of homologous recombination and DNA repair are not well understood in eukaryotes. In lower eukaryotes such as yeast, a number of DNA repair mechanisms exist. For example, in yeast, three epistasis groups of DNA damage-repair genes have been identified (see Friedberg et al., in The Molecular and Cellular Biology of the Yeast Saccharomyces, Broach et al. Eds., pp 147–192, 1991 Cold Spring Harbor Laboratory Press, Cold Spring Harbor, N.Y.). However, in higher eukaryotes, the identification, characterization and interaction of the relevant proteins is largely unknown.

The present invention is based on the finding that human Rad52 will bind to nucleic acid to effect strand annealing and strand exchange. Thus, the present invention provides compositions comprising complexes of nucleic acids and isolated Rad52 from a higher eukaryote.

In a preferred embodiment, the invention provides a first single stranded nucleic acid complexed with isolated Rad52 from a higher eukaryote. As used herein, "nucleic acid" or "oligonucleotide" means at least two nucleotides linked together, and may refer to either DNA or RNA, or molecules which contain both deoxy-and ribo-nucleotides. The nucleic acids include mRNA, genomic DNA, cDNA and oligonucleotides including sense and anti-sense nucleic acids. "Nucleic acid" also includes nucleic acid analogs, such as nucleic acids that contain modifications in the ribose-phosphate backbone to increase stability and half life of such molecules in physiological environments. For example, a nucleic acid of the present invention will generally contain phosphodiester bonds, although in some cases, as outlined below, a nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate, phosphorodithioate, O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Nucleic acids containing one or more carbocyclic sugars are also included within the definition of nucleic acids (see Jenkins et al., Chem. Soc. Rev. (1995) pp169–176). These modifications of the ribose-phosphate backbone may be done to increase the stability and half-life of such molecules in physiological environments.

Unless specified, the nucleic acid may be double stranded, single stranded, or contain portions of both double stranded or single stranded sequence. By the term "recombinant nucleic acid" herein is meant nucleic acid, originally formed in vitro, in general, by the manipulation of nucleic acid by endonucleases, in a form not normally found in nature. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

In a preferred embodiment, the nucleic acids of the invention range in size from about 10 base pairs to about 100 base pairs, with from about 20 to about 80 base pairs being preferred, although as will be appreciated by those in the art, much longer nucleic acids may be used as well.

The nucleic acids are complexed with isolated Rad52 protein from a higher eukaryote. By "complexed" herein is meant that the Rad52 protein binds to or forms a non-covalent association with the nucleic acid. Preferably, the complex is stable to electrophoretic conditions. In one embodiment, the complex comprises the nucleic acid with at least one associated Rad52 protein. In a preferred embodiment, a plurality of proteins are associated to form the complex. Thus for example, preferred embodiments utilize ratios of protein to nucleotide ranging from about 1:1 to about 1:10, with from about 1:1 to about 1:5 being preferred and from about 1:1 to about 1:2 being especially preferred. Thus, in a preferred embodiment, the nucleic acid is substantially coated with Rad52 protein.

By "Rad52 protein" herein is meant a Rad52 protein from a higher eukaryote. By "higher eukaryote" herein is meant a multicellular organism, including, but not limited to, plants and vertebrates such as birds, fish and mammals. Higher eukaryotes do not include lower eukaryotes such as yeast and fungi. Preferred higher eukaryotes include, but are not limited to, plants, birds, fish and mammals, with chicken, goats, cows, rodents such as mice and rats, salmon, and mammals being particularly preferred. Humans are particularly preferred.

Rad52 proteins are identified as having two characteristics: (1) Rad52 proteins have significant homology to the N-terminus of known Rad52 proteins, including chicken, mouse and human; and (2) Rad52 proteins will mediate annealing and strand exchange, as described herein.

Rad52 proteins may be initially identified by homology to other higher eukaryotic Rad52 proteins, including chicken, mouse and human (see Park, J. Biol. Chem. 270:15467–15470 (1995); Muris et al., Mutation Res., DNA Repair 315:295–305 (1994); Bezzubova et al., Nucleic Acid Res. 21(25):5945–5949 (1993); Bendixen et al., Genomics 23:300–303 (1994); Shen et al., Genomics 25:199–206 (1995), all of which are expressly incorporated by reference). As noted above, the N-terminus of Rad52 is highly conserved among species; in the N-terminus, chicken Rad52 is roughly 90% homologous to both human Rad52 and mouse Rad52, and mouse Rad52 is roughly 99% homologous to human Rad52. Thus, proteins with significant homology to the N-terminus of known Rad52 proteins are considered Rad52 proteins. The highly homologous N-terminus comprises from about amino acid 36 to about amino acid 185, using the human Rad52 sequence numbering (see Muris et al., supra). All or part of this sequence may be used to identify Rad52 proteins.

Thus, as used herein, a protein is a "Rad52 protein" if the overall homology of the protein sequence to the N-terminal amino acid sequences of human, chicken or mouse Rad52 is preferably greater than about 50%, more preferably greater than about 60% and most preferably greater than 75%. In some embodiments the homology will be as high as about 90 to 95 or 98%. This homology will be determined using standard techniques known in the art, such as the Best Fit sequence program described by Devereux et al., Nucl. Acid Res. 12:387–395 (1984) or the BLASTX program (Altschul et al., J. Mol. Biol. 215, 403–410). The alignment may include the introduction of gaps in the sequences to be aligned. In addition, for sequences which contain either more or fewer amino acids than these proteins, it is understood that the percentage of homology will be determined based on the number of homologous amino acids in relation to the total number of amino acids. Thus, for example, homology of sequences shorter than those of the known Rad52 proteins, as discussed below, will be determined using the number of amino acids in the shorter sequence.

With respect to the C-terminal sequence of Rad52, different species show a marked lack of homology in this region, and thus this area is not suitable for definition of a Rad52 protein. In some embodiments, all or part of the C-terminus may be deleted, although this area is postulated to interact with other Rad proteins such as Rad51 and RPA, and thus may be important.

Rad52 proteins useful in the present invention may be shorter or longer than the known Rad52 sequences, as long as the protein has both sequence and functional homology to the N-terminus of known Rad52 sequences.

In a preferred embodiment, the Rad52 protein is recombinant. A "recombinant protein" is a protein made using recombinant techniques, i.e. through the expression of a recombinant nucleic acid as depicted above. A recombinant protein is distinguished from naturally occurring protein by at least one or more characteristics. For example, the protein may be isolated or purified away from some or all of the proteins and compounds with which it is normally associated in its wild type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of a Rad52 protein from one organism in a different organism or host cell. Alternatively, the protein may be made at a significantly higher concentration than is normally seen, through the use of a inducible promoter or high expression promoter, such that the protein is made at increased concentration levels. Alternatively, the protein may be in a form not normally found in nature, as in the addition of an epitope tag, a purification signal such as $His_6$, or amino acid substitutions, insertions and deletions, as discussed below.

Also included with the definition of Rad52 proteins are Rad52 proteins from other organisms, which are cloned and expressed as outlined below. Thus, probe or degenerate polymerase chain reaction (PCR) primer sequences may be used to find other related Rad52 proteins from other organisms. As will be appreciated by those in the art, particularly useful probe and/or PCR primer sequences include the unique areas of the Rad52 nucleic acid sequence. Thus, useful probe or primer sequences may be designed to all or part of the N-terminal sequence of the known Rad52 sequences. As is generally known in the art, preferred PCR primers are from about 15 to about 35 U.S.C. § nucleotides in length, with from about 20 to about 30 being preferred, and may contain inosine as needed. The conditions for the PCR reaction are well known in the art.

Once the Rad52 nucleic acid is identified, it can be cloned and, if necessary, its constituent parts recombined to form the entire Rad52 nucleic acid. Once isolated from its natural source, e.g., contained within a plasmid or other vector or excised therefrom as a linear nucleic acid segment, the recombinant Rad52 nucleic acid can be further used as a probe to identify and isolate other Rad52 nucleic acids. It can also be used as a "precursor" nucleic acid to make modified or variant Rad52 nucleic acids and proteins as is more fully described below.

Using the nucleic acids of the present invention which encode a Rad52 protein, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the Rad52 protein. "Operably linked" in this context means that the transcriptional and translational regulatory DNA is positioned relative to the coding sequence of the Rad52 protein in such a manner that transcription is initiated. Generally, this will mean that the promoter and transcriptional initiation or start sequences are positioned 5' to the Rad52 protein coding region. The transcriptional and translational regulatory nucleic acid will generally be appropriate to the host cell used to express the Rad52 protein; for example, transcriptional and translational regulatory nucleic acid sequences from Bacillus are preferably used to express the Rad52 protein in Bacillus. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention.

In addition, the expression vector may comprise additional elements. For example, the expression vector may have two replication systems, thus allowing it to be maintained in two organisms, for example in mammalian or insect cells for expression and in a procaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

The Rad52 proteins of the present invention are produced by culturing a host cell transformed with an expression vector containing nucleic acid encoding a Rad52 protein, under the appropriate conditions to induce or cause expression of the Rad52 protein. The conditions appropriate for Rad52 protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archebacteria, fungi, and insect and animal cells, including mammalian cells. Of particular interest are *Drosophila melangaster* cells, *Saccharomyces cerevisiae* and other yeasts, *E. coli, Bacillus subtilis,* SF9 cells, C129 cells, 293 cells, Neurospora, BHK, CHO, COS, and HeLa cells, fibroblasts, Schwanoma cell lines, stem cells, bone marrow and immortalized mammalian myeloid and lymphoid cell lines.

In a preferred embodiment, the Rad52 proteins are expressed in mammalian cells. Mammalian expression systems are also known in the art. A mammalian promoter is any DNA sequence capable of binding mammalian RNA polymerase and initiating the downstream (3') transcription of a coding sequence for Rad52 protein into mRNA. A promoter will have a transcription initiating region, which is usually placed proximal to the 5' end of the coding sequence, and a TATA box, using a located 25–30 base pairs upstream of the transcription initiation site. The TATA box is thought to direct RNA polymerase II to begin RNA synthesis at the correct site. A mammalian promoter will also contain an upstream promoter element (enhancer element), typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenylation signals include those derived form SV40.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, encapsulation of the polynucleotide (s) in liposomes, and direct microinjection of the DNA into nuclei.

In a preferred embodiment, Rad52 proteins are expressed in bacterial systems. Bacterial expression systems are well known in the art.

A suitable bacterial promoter is any nucleic acid sequence capable of binding bacterial RNA polymerase and initiating the downstream (3') transcription of the coding sequence of Rad52 protein into mRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of nonbacterial origin that have the ability to bind bacterial RNA polymerase and initiate transcription.

In addition to a functioning promoter sequence, an efficient ribosome binding site is desirable. In *E. coli,* the ribosome binding site is called the Shine-Dalgarno (SD) sequence and includes an initiation codon and a sequence 3–9 nucleotides in length located 3–11 nucleotides upstream of the initiation codon.

The expression vector may also include a signal peptide sequence that provides for secretion of the Rad52 protein in bacteria. The signal sequence typically encodes a signal peptide comprised of hydrophobic amino acids which direct the secretion of the protein from the cell, as is well known in the art. The protein is either secreted into the growth media (gram-positive bacteria) or into the periplasmic space, located between the inner and outer membrane of the cell (gram-negative bacteria).

The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways.

These components are assembled into expression vectors. Expression vectors for bacteria are well known in the art, and include vectors for *Bacillus subtilis, E. coli, Streptococcus cremoris,* and *Streptococcus lividans,* among others.

The bacterial expression vectors are transformed into bacterial host cells using techniques well known in the art, such as calcium chloride treatment, electroporation, and others.

In one embodiment, Rad52 proteins are produced in insect cells. Expression vectors for the transformation of insect cells, and in particular, baculovirus-based expression vectors, are well known in the art.

In a preferred embodiment, Rad52 protein is produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K lactis, Pichia guillerimondii* and *P. pastoris, Schizosaccharomyces pombe,* and *Yarrowia lipolytica.* Preferred promoter sequences for expression in yeast include the inducible GAL1, 10 promoter, the promoters from alcohol dehydrogenase, enolase, glucokinase, glucose-6-phosphate isomerase, glyceraldehyde-3-phosphate-dehydrogenase, hexokinase, phosphofructokinase, 3-phosphoglycerate mutase, pyruvate kinase, and the acid phosphatase gene. Yeast selectable markers include ADE2, HIS4, LEU2, TRP 1, and ALG7, which confers resistance to tunicamycin; the neomycin phosphotransferase gene, which confers resistance to G418; and the CUP1 gene, which allows yeast to grow in the presence of copper ions.

The Rad52 protein may also be made as a fusion protein, using techniques well known in the art. Thus, for example, the Rad52 protein may be made as a fusion protein to increase expression, or for other reasons. For example, when the Rad52 protein is a Rad52 peptide, the nucleic acid encoding the peptide may be linked to other nucleic acid for expression purposes.

Also included within the definition of Rad52 proteins of the present invention are amino acid sequence variants. These variants fall into one or more of three classes: substitutional, insertional or deletional variants. These variants ordinarily are prepared by site specific mutagenesis of nucleotides in the DNA encoding the Rad52 protein, using cassette or PCR mutagenesis or other techniques well known in the art, to produce DNA encoding the variant, and thereafter expressing the DNA in recombinant cell culture as outlined above. However, variant Rad52 protein fragments having up to about 100–150 residues may be prepared by in vitro synthesis using established techniques. Amino acid sequence variants are characterized by the predetermined nature of the variation, a feature that sets them apart from naturally occurring allelic or interspecies variation of the Rad52 protein amino acid sequence. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed Rad52 variants screened for the optimal combination of desired activity. Techniques for making substitution mutations at predetermined sites in DNA having a known sequence are well known, for example, M13 primer mutagenesis and PCR mutagenesis. Screening of the mutants is done using assays of Rad52 protein activities; for example, for binding domain mutations, competitive binding studies such as are outlined in the Examples may be done.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the Rad52 protein are desired, substitutions are generally made in accordance with the following chart:

Chart I

| Original Residue | Exemplary Substitutions |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Chart I. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

The variants typically exhibit the same qualitative biological activity and will elicit the same immune response as the naturally-occurring analogue, although variants also are selected to modify the characteristics of the Rad52 proteins as needed. Alternatively, the variant may be designed such that the biological activity of the Rad52 protein is altered. For example, regions involved in DNA binding or other protein—protein interactions (such as Rad51, etc.) may be altered.

In one embodiment, the nucleic acids and/or Rad52 proteins of the invention are labeled. By "labeled" herein is meant that a compound has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the complex at any position.

In a preferred embodiment, the Rad52 protein is purified or isolated after expression. Rad52 proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the Rad52 protein may be purified using a standard anti-Rad52 antibody column. If purification sequences are included, such as the $His_6$ tag, suitable methods are used, such as a metal-containing column. Ultrafiltration and diafiltration techniques, in conjunction with protein concentration, are also useful. For general guidance in suitable purification techniques, see Scopes, R., Protein Purification, Springer-Verlag, N.Y. (1982).

Once expressed and purified if necessary, the Rad52 proteins are complexed with the desired nucleic acid. Generally, this is done by adding the isolated Rad52 proteins with nucleic acids, as outlined herein. As outlined above, the amount of Rad52 protein added to the nucleic acid can vary. Preferred embodiments utilize a 1:1 ratio of protein to nucleotide within the nucleic acid; i.e. 10 molecules of Rad52 for a nucleic acid 10 nucleotides in length.

Binding of Rad52 to nucleic acid may be verified by gel migration studies, as will be appreciated by those in the art and outlined in the Examples.

It should be noted that the mechanism of binding of Rad52 protein to nucleic acid is both ATP and $Mg+2$ independent. That is, unlike RecA or Rad5 1 binding to nucleic acid, Rad52 protein is able to bind to nucleic acid in the absence of co-factors or specific ions.

In a preferred embodiment, the isolated Rad52 protein is complexed to a first single stranded nucleic acid, as outlined herein. This complex is capable of mediating the annealing of this first single stranded nucleic acid to a complementary single stranded nucleic acid. Thus Rad52 proteins are defined functionally as well. By "mediating" herein is meant that the presence of the Rad52 protein will either (1) allow annealing of two pieces of nucleic acid which in the absence of the Rad52 would not spontaneously anneal under the reaction conditions; or (2) will increase the rate at which annealing occurs. Thus, the Rad52 protein/nucleic acid complex is recombination active, i.e. able to anneal, or do strand exchange, or both.

Thus, for example, it has been shown that the presence of some types and number of mismatches as between two single stranded nucleic acids will prevent spontaneous annealing (see for example Panyutin et al., J. Mol. Biol. 230:413–424 (1993), hereby expressly incorporated by reference). Similarly, the presence of certain buffer conditions, even in the absence of mismatches, will prevent or reduce spontaneous annealing (see the Examples). Thus, in the presence of Rad52, the rate at which the single stranded nucleic acids will anneal is faster than the rate (if any) in the absence of Rad52.

Annealing is done with complementary nucleic acids. By "complementary" herein is meant one of two things. In a preferred embodiment, the two single stranded nucleic acids are sufficiently complementary to hybridize or anneal under at least low stringency conditions, with complementarity preferably being sufficient to allow hybridization under moderate or high stringency conditions. Generally, low, moderate and high stringency conditions are known in the art. Suitable representative low, moderate and high stringency conditions are known in the art.

Additionally or alternatively, complementary means that the two single stranded nucleic acids are at least sufficiently complementary to be capable of base pairing in the presence of Rad52. That is, since Rad52 mediates the annealing of single stranded nucleic acids that would not ordinarily anneal, nucleic acids which do not spontaneously anneal or do so only very slowly, such that they would not normally be considered "complementary" are considered complementary for the purposes of this application if they will anneal in the presence of Rad52 protein.

Thus, complementary nucleic acids may be: perfectly complementary, i.e. contain no mismatches; significantly complementary, i.e. contain from less than about 1% to about 10% mismatches; or minimally complementary, i.e. contain roughly about 10 to 30 or 40% mismatches, but still be sufficiently complementary to allow annealing in the presence of Rad52 protein.

The compositions of the invention may further comprise a second single stranded nucleic acid complexed to Rad52 protein. In a preferred embodiment, this second single stranded nucleic acid is complementary, as defined above, to the first single stranded nucleic acid with bound Rad52.

The compositions of the present invention may comprise other elements, such as other proteins, or specific binding moieties for purification or assay purposes.

In a preferred embodiment, the invention provides methods of accomplishing strand exchange. In this embodiment, the compositions of the invention comprise a first single stranded nucleic acid complexed with Rad52, and a double stranded nucleic acid comprising a second and a third single stranded nucleic acid. In this embodiment, the first and third single stranded nucleic acids are complementary to the second nucleic acid, such that strand exchange between the third and first nucleic acids may occur. Thus, the third nucleic acid is displaced from the double stranded nucleic acid and replaced by the first nucleic acid, with annealing of the first and second nucleic acids, to provide a double stranded nucleic acid comprising the first and second nucleic acids, leaving the third nucleic acid as a single stranded nucleic acid.

The invention also provides methods of making double stranded nucleic acid comprising contacting a first single stranded nucleic acid, a second single stranded nucleic acid, and isolated Rad52 protein from a higher eukaryote. This contacting may be done in any order. For example, in a preferred embodiment, the first or the second nucleic acid and the Rad52 proteins may be contacted first, forming a nucleic acid-Rad52 complex, followed by addition of the other nucleic acid, which leads to annealing of the first and second nucleic acids to form a double stranded nucleic acid. Alternatively, the first and second nucleic acids may be added, followed by the addition of the Rad52 protein. Assays to measure whether annealing has been accomplished are well known in the art.

In a preferred embodiment, the compositions of the invention are used in screening assays for bioactive agents involved in homologous recombination. In this embodiment, candidate bioactive agents are added to the compositions of the invention. By "candidate bioactive agent" herein is meant any molecule, e.g. proteins, including antibodies, oligopeptides, small organic molecule, polysaccharide, polynucleotide, etc., which may be tested for the ability to alter the bioactivity of the composition. Particularly preferred candidate bioactive agents are proteins, and particularly preferred are other Rad52 epistasis group proteins.

In one embodiment, the method consists of adding a candidate bioactive agent, a first single stranded nucleic acid, and isolated Rad52 protein, to form a mixture. The addition may be done in any order. In a preferred embodiment, the first nucleic acid and the Rad52 protein are complexed prior to the addition of the candidate agent. Alternatively, the components are added simultaneously, or the candidate agent is added first to either the first nucleic acid or the Rad52 protein. The mixture is then assayed for altered biological activity.

By "bioactivity" or "biological activity" herein is meant any of a number of potential biological activities of the compositions of the invention. Biological activity includes, but is not limited to, nucleic acid binding, annealing, strand-exchange, and homology scanning. Generally, the biological activity will be tested using well known procedures. By "altered biological activity" herein is meant that the biological activity of the mixture of the candidate bioactive agent and the Rad52-protein complex is different, i.e. increased or decreased, relative to the biological activity in the absence of the candidate agent.

In one embodiment the desired bioactivity is binding to the complex of Rad52 and nucleic acid. Thus, in this embodiment, the screening assay is a binding assay; that is, the desired bioactivity is binding to nucleic acid, either in the presence of Rad52, i.e. binding to the Rad52-nucleic acid complex, or to prevent Rad52 binding. In this embodiment, one or more of the molecules may be joined to a label, where the label can directly or indirectly provide a detectable signal. Alternatively, the determination of binding activity is done via gel mobility studies.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference.

EXAMPLES

Materials. T4 phage DNA ligase and restriction enzyme (Not I) were obtained from New England Biolabs, Ma., USA. AmpliTaq ploymerase was from Perkin-Elmer, Conn., USA. Expand High Fidelity PCR Kit was from Boehringer Mannheim Co, Ind., USA. Expression vector pQE-31, E. coli M15 (pREP4) strain, Probond nickel matrix was obtained from Invitrogen, Calif., USA.

Cloning of the HsRad52 gene. The whole coding sequence of human Rad52 (HsRad52) was amplified by PCR from human thymus cDNA library. Sequences of the upstream and downstream primers are EG182: CGCG-GATCCGATGTCT GGGACTGAGGAAGCAA [SEQ ID NO: 1] and EG225: GTAGGATCCTGAGCCTCAGT-TAAG ATGG [SEQ ID NO: 2]. Underlined sequences are homologous to the published 5' end and 3' end sequence of the HsRad52 gene (10, 12). For PCR, 0.5 $\mu$g of DNA was used in mixture containing each primer at 200 nM, 10 mM Tris-HCl (pH 8.3), 50 mM KCl 1 mM MgCl2, 0.01% gelatin, each of the four dNTP's at 200 $\mu$M and 2.5 units of AMPLITA Q ploymerase. The reaction mixture was heated at 95° C. for 3 min and used in a PCR consisting of 30 cycles of 94° C. for 1 min, 6° C. for 1 min, and 72° C. for 1 min. The resulting DNA fragment was labeled with [ -32P] dCTP by random priming (24) and used as a probe for isolation of a HsRad52 clone from human testis cDNA library in lambda Charon BS phage (25). DNA isolated from a hybridization-positive clone was digested by Not I and treated with T4 DNA ligase. The ligation mixture was used for transformation of E. coli SY204. Ampicilin resistant transformants contained a plasmid, designated pEG970, which carries HsRad52 cDNA. The plasmid was used as a template for amplification of the coding region of HsRad52 gene by PCR reaction. The reaction was carried out by using Expand High Fidelity PCR Kit and primers EG182 and EG225. The resulting DNA fragment was inserted into expression vector pQE-31 in frame with 5' end sequence coding for a series of six histidine residues that function as a metal-binding domain in the translated fusion protein.

Isolation of HsRad52 protein. Plasmid pEG2 which carries the whole coding sequence of the HsRad52gene in the vector pQE-31 was introduced into E. coli M15 (pREP4). Synthesis of the protein is under the control of the E. coli phage T5 promoter and two lac operator sequences and can be induced by β-D-thiogalactopyranoside 00(IPTG). For the isolation of HsRad52 protein, E. coli M15 (pREP4)/pEG2 cells were grown in LB medium at 37° C. to OD590=0.6 and induced with 2 mM IPTG. Cells were harvested 2 hrs after induction and resuspended in buffer containing 50 mM Tris-HCl (pH8.0), 10% sucrose. Cells were lysed by the addition 10 mg/ml of lysozyme. Solution was kept on ice and stirred for 30 min, then 350 mM KCl and 0.5% Brij 58 were added and stirred on ice for another 60 min. Cell debris was spun down by centrifugation at 35000 rpm for 75 min at 4° C. HsRad52 protein from the supernatant was loaded directly on PROBOND nickel column, that was equilibrated with 50 mM Tris-HCl (pH 8.0), 300 mM NaCl. The column was washed with 20 volumes of washing buffer (50 mM Tris-HCl (pH 6.0), 300 mM NaCl, 50 mM imidazole) and the bound protein was eluted with 50 mM Tris-HCl (pH 6.0), 300 mM NaCl and 500 mM imidazole. Peak fractions were dialyzed against 50 mM Tris-HCl (pH 8.0), 200 mM NaCl and 10% glycerol. The purified protein was near homogeneous (FIGURE 1) and did not contain any detectable nucleases under the reaction conditions.

Binding of HsRad52 protein to single-stranded and double-stranded DNA. The DNA binding activity of HsRad52 protein was determined by band shift assay. The reaction mixtures (10 μL) contained 20 mM Tris-HCl (pH 8.0), 1 mM MgC12, 75 mM NaCl, 10 mM β-mercatoethanol, 1 μM DNA and 1 μM HsRAD52 protein. The reaction mixtures with or without HsRad52 protein were incubated at 37° C. for 30 min and were electrophoresed on 0.8% agarose gel. The gels were subsequently dried and examined by autoradiography. Single-stranded DNA used in this experiment was a 43-mer oligonucleotide, end labeled with 32 -g ATP using polynucleotide kinase. Blunt ended double-stranded was obtained by thermally annealing a complementary 43 to the labeled 43-mer oligonucleotide. Similarly, partial duplexes with 3' tail or 5' tail were obtained by thermally annealing the labeled 43-mer with a complementary 63-mer oligonucleotide which has an additional 20 nucleotides at the 3' end or 5' end. HsRad52 protein bound equally efficiently to single-stranded DNA, double-stranded DNA and partial duplexes with 3' or 5' overhanging tails (data not shown). All of the DNA was bound by HsRad52 protein and the resulting protein-DNA complex moved slowly in 0.8% agarose gel (data not shown). The binding of HsRad52 protein was optimal at 1:1 ratio of protein to nucleotide concentrations. At lower concentrations of protein (one protein for every two or four nucleotides) binding was incomplete and resulted in a band that was smeared (data not shown).

In order to detect the ability of HsRad52 protein to anneal complementary strands of DNA and also to assess its role in branch migration/strand exchange, we used an assay described by Panyutin and Hsieh, supra. HsRad52 promotes annealing. The design of the experiments is shown in FIGURE 1. Reactions were carried out with a partial duplex made by annealing 32P-labeled oligonucleotide 43-mer to M13, a 12.5-fold molar excess of donor oligonucleotide with respect to the number of molecules of M13 single stands and a molar ratio of 1:1.5 of HsRad52 protein with respect to the nucleotide residues of the donor oligonucleotide. Reaction mixtures (10 μL) contained 20 mM Tris-HCl at pH 8.0, 20 mM Nacl, 10 mM 62-mercapto ethanol 0.6 μM of 63-mer and 0.4 μM of HsRad52. Reaction mixtures were preincubated at 37° C. for 15 min followed by the addition of 5 μM of M13/43/-mer partial duplex and the reactions were incubated at 37° C. for a further 60 min. After the incubation reactions mixtures were deproteinized with the addition of 0.1 mg/mL proteinase K, 0.5% SDS at 37° C. for 15 min. Samples were analyzed by gel electrophoresis on 0.8% agarose gels, and quantitated by phosphorimaging. Conditions for all the control reactions were the same as with HsRad52 protein.

A 43-mer oligonucleotide radiolabeled at its 5' end was annealed to single-stranded circular M13 DNA to form a partial duplex (called as M13/43-mer duplex) Displacement of the labeled 43-mer by a longer, overlapping, unlabeled 63-mer (called as donor strand) requires first the the donor oligonucleotide anneal to one side of the partial duplex region, followed by a strand exchange reaction. Depending on conditions, annealing, strand exchange, or both may occur spontaneously or by a catalyzed reaction. The uncatalyzed reaction is usually called as branch migration.

Using such substrates, Panyutin and Hsieh (supra) previously studied spontaneous branch migration in reaction mixtures that contained 50 mM Tris-HCl (pH 7.5), 50 mM NaCl and a 250-fold excess of the donor oligonucleotide. They found that 4 mismatches largely blocked the uncatalyzed reaction. Alternatively, spontaneous branch migration is reduced significantly, even in the absence of mismatches, when the reaction conditions are as follows: 20 mM Tris-HCl (pH 7.5 or 8.0), 20 mM Nacl and a 25-fold molar excess of the overlapping single-stranded oligonucleotide. These conditions were used for studying the action of HsRad52 protein.

The donor oligonucleotide was incubated with HsRad52 under the conditions just described for 10 min and added the partial duplex to start the strand displacement reaction. HsRad52 promoted the displacement of the 43-mer oligonucleotide from the M13/43-mer duplex by a fully homologous 63-mer that had 20 extra nucleotide residues at its 5' end as determined on gels. Displacement was minimal in the absence of HsRad52, did not occur in the absence of 63-mer oligonucleotide, or when the oligonucleotide was heterologous. Displacement also did not occur when the oligonucleotide was homologous only at its overhanging 5' end, indicating that displacement depends upon replacement of one homologous strand by another, rather than on a helicase activity of HsRad52 protein. However, presence of 4 mismatches in the 63-mer oligonucleotide reduced the strand displacement to roughly about 10%. The efficiency of this reaction could be increased to about 24% by increasing the concentration of the invading oligonucleotide to 50-fold molar excess (data not shown). Displacement of the 43-mer oligonucleotide from the partial duplex occured even when the order of addition was reversed i.e. when the HsRad52 was first incubated with the partial duplex and the donor was added later to start the reaction (data not shown).

We claim:

1. A composition comprising a complex of a first single stranded nucleic acid and isolated Rad52 protein from a higher eukaryote.

2. A composition according to claim 1 wherein said complex mediates the annealing of said first nucleic acid to a complementary second single stranded nucleic acid.

3. A composition according to claim 1 wherein said Rad52 protein is a mammalian Rad52 protein.

4. A composition according to claim 1 wherein said Rad52 protein is a human Rad52 protein.

5. A composition according to claim 1 further comprising a double stranded nucleic acid comprising second and third single stranded nucleic acids, wherein both said first and said third nucleic acids are complementary to said second nucleic acid.

6. A composition according to claim 1 further comprising a second single stranded nucleic acid complexed with isolated Rad52 protein from a higher eukaryote.

7. A composition according to claim 6 wherein said second nucleic acid is complementary to said first nucleic acid.

8. A method of making double stranded nucleic acid comprising contacting:
    a) a first single stranded nucleic acid;
    b) a second single stranded nucleic acid, wherein said first and second nucleic acids are complementary; and
    c) isolated Rad52 protein from a higher eukaryote;
under conditions whereby said Rad52 mediates annealing of said first and second nucleic acids.

9. A method according to claim 8, wherein one or both of said nucleic acids are complexed with said isolated Rad52 protein prior to said contacting.

10. A method according to claim 8, wherein said annealing is done in the absence of $Mg^{+2}$ and cofactors.

11. A method of accomplishing strand exchange comprising contacting:
    a) a first single stranded nucleic acid;
    b) a double stranded nucleic acid comprising second and third single stranded nucleic acids, wherein both said first and third nucleic acids are complementary to said second nucleic acid; and
    c) isolated Rad52 from a higher eukaryote;
under conditions whereby said Rad52 mediates the annealing of said first nucleic acid to said second nucleic acid, such that said third nucleic acid is displaced.

12. A method according to claim 11 wherein any or all of said nucleic acids are complexed with said Rad52 prior to said contacting.

13. A method according to claim 11, wherein said annealing is done in the absence of $Mg^{+2}$ and cofactors.

14. A method according to claim 11 wherein said Rad52 protein is a mammalian Rad52 protein.

15. A method according to claim 11 wherein said Rad52 protein is a human Rad52 protein.

16. A method of screening for a bioactive agent involved in homologous recombination comprising:
    a) contacting:
        i) a candidate bioactive agent;
        ii) a first single stranded nucleic acid; and
        iii) isolated Rad52 protein from a higher eukaryote; and
    b) screening for binding of said candidate and said Rad52 to said nucleic acid.

17. A method according to claim 16 wherein said first nucleic acid and said isolated Rad52 are complexed prior to the addition of said candidate agent.

18. A method according to claim 16 wherein said Rad52 protein is a mammalian Rad52 protein.

19. A method according to claim 16 wherein said Rad52 protein is a human Rad52 protein.

20. A method of screening for a bioactive agent involved in homologous recombination comprising:
    a) adding:
        i) a candidate bioactive agent;
        ii) a first single stranded nucleic acid; and
        iii) isolated Rad52 protein from a higher eukaryote to form a mixture; and
    b) screening said mixture for altered biological activity, when compared to the biological activity of said composition in the absence of said candidate.

21. A method according to claim 20 wherein said first nucleic acid and said isolated Rad52 are complexed prior to the addition of said candidate agent.

22. A method according to claim 20 wherein said Rad52 protein is a mammalian Rad52 protein.

23. A method according to claim 20 wherein said Rad52 protein is a human Rad52 protein.

* * * * *